United States Patent [19]

Swithenbank

[11] Patent Number: 4,743,703

[45] Date of Patent: May 10, 1988

[54] HERBICIDAL 4-FLUOROALKYL-4'-NITRODIPHENYL ETHERS

[75] Inventor: Colin Swithenbank, Perkasie, Pa.

[73] Assignee: Rohm and Haas Company, Philadelphia, Pa.

[21] Appl. No.: 533,275

[22] Filed: Sep. 19, 1983

Related U.S. Application Data

[63] Continuation-in-part of Ser. No. 312,456, Oct. 19, 1981.

[51] Int. Cl.$^4$ .............................................. C02C 79/46
[52] U.S. Cl. ...................................... 560/21; 562/435;
564/171; 564/340; 564/347; 558/412; 558/414;
558/416; 568/637; 568/638; 71/107; 71/114
[58] Field of Search .................. 560/21; 562/435, 633;
564/171; 558/412, 414, 416; 71/107, 114

[56] References Cited

FOREIGN PATENT DOCUMENTS 2076393A 12/1981 United Kingdom .

*Primary Examiner*—Paul J. Killos
*Attorney, Agent, or Firm*—Polly E. Ramstad

[57] ABSTRACT

The 4-fluoroalkyl-4'-nitrodiphenyl ethers comprise a class of compounds that are highly effective herbicides.

20 Claims, No Drawings

HERBICIDAL 4-FLUOROALKYL-4'-NITRODIPHENYL ETHERS

CROSS-RELATED APPLICATION

This application is a continuation-in-part of U.S. application Ser. No. 312,456 filed Oct. 19, 1981.

BACKGROUND OF THE INVENTION

1. Field of the Invention

This invention is concerned with substituted diphenyl ethers and their use as herbicides.

2. Description of the Prior Art

It has been proposed to use as herbicides 2-methoxybenzoic acids (U.S. Pat. No. 3,013,054), 4-phenoxybenzoic acids (French Pat. No. 1,502,538), substituted phenoxybenzoic acids (U.S. Pat. Nos. 3,979,437 and 4,164,409) and certain 4-trifluoromethyl-4'-nitrodiphenyl ethers (U.S. Pat. Nos. 3,928,416, 4,046,798, and 4,063,929). It is the discovery of this invention, however, that cetain 4-fluorinated higher alkyl-4'nitrodiphenyl ethers are very effective herbicides.

SUMMARY OF THE INVENTION

This invention provides herbicidal compounds having the formula

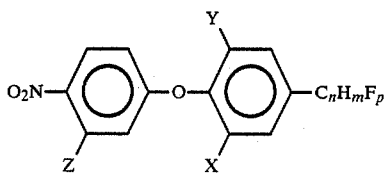

(I)

wherein n is an integer of from 1 through 5, m is an integer of from 0 through 2n, p is an integer of from 1 through $2n+1$, $m+p=2n+1$, X is a hydrogen atom, a halogen atom, preferably a fluorine atom or a chlorine atom, a trihalomethyl group, preferably a trifluoromethyl group, a $(C_1-C_4)$alkyl group, preferably a methyl group, or a cyano group, Y is a hydrogen atom, a halogen atom, preferably a fluorine atom or a chlorine atom, or a trifluoromethyl group, preferably a trifluoromethyl group, and Z is a hydroxy group, an alkoxy group, preferably having 1 to 6 carbon atoms, and most preferably 1 to 4 carbon atoms, an alkyl group, preferably having 1 to 4 carbon atoms, a halogen atom, preferably a chlorine atom or a fluorine atom, an amino group, preferably having up to 6 carbon atoms, an alkylthio group, preferably having 1 to 4 carbon atoms, a cyano group, a carboxy group or an agronomically-acceptable salt thereof, preferably sodium, potassium or ammonium, a carbalkoxy group, —CO$_2$R, preferably having 1 to 4 carbon atoms in the alkoxy moiety, a carboxyalkyl group, —R'-CO$_2$H, preferably having up to 4 carbon atoms, a carbalkoxyalkyl group, —R'CO$_2$R, preferably having up to 6 carbon atoms, an alkanoyloxy group, —OCOR, preferably having up to 4 carbon atoms, optionally substituted with a halogen atoms, or a carboamoyloxy group, —OCONH$_2$, —OCONHR, or —OCONR$_2$, preferably having up to 6 carbon atoms.

In the above definitions of the Z substituent, R represents an alkyl group, and R' represents a divalent alkylene group. The alkyl or alkylene portion of the alkyl-containing X and Z substituents can have either a straight- or branched-chain or a cyclic spatial configuration.

As used in the present specification and claims, the term "alkoxy group" is intended to include both unsubstituted alkoxy groups as well as substituted alkoxy groups which have one or more of the hydrogen atoms replaced by a substituent group. Among the substituted alkoxy groups which Z can represent are alkoxy groups of preferably up to 4 carbon atoms substituted with a halogen atom, a hydroxy group, a $(C_1-C_4)$alkoxy group, a carboxy group, or an agronomically-acceptable salt thereof, preferably sodium, potassium, or ammonium, a carbalkoxy group, preferably up to 4 carbon atoms in the ester alkoxy group, a trihaloalkyl group, preferably a trifluoromethyl group, an alkenyl group, an alkynyl group, preferably an ethynyl group, an amino group, an alkyl- or dialkylamino group, including heterocyclic substituents such as morpholino, piperazino, piperidino, and the like, and preferably having a total of up to 4 carbon atoms, an alkylthio group, preferably having up to 4 carbon atoms, an alkylsulfonyl group, preferably having up to 4 carbon atoms, an epoxy group, an alkylcarbonyl group, including halo-substituted alkylcarbonyl, and preferably having up to 4 carbon atoms in the alkyl group, most preferably methylcarbonyl, a carbamoyl group, including alkyl- or dialkylcarbamoyl, preferably having a total of up to 4 carbon atoms in the alkyl substituents.

The term "amino group" as used in the present specification and claims is intended to include an unsubstituted amino group, —NH$_2$, as well as amino groups having one or both hydrogen atoms replaced by substituent groups. Among the substituted amino groups which Z can represent are amino groups substituted with one or two alkyl groups, preferably having a total of up to 6 carbon atoms, halo-, hydroxy-, or alkoxy-substituted alkyl groups, preferably having a total of up to 6 carbon atoms, one or two alkylthio carbonyl groups, preferably having a total of up to 4 carbon atoms in the alkyl moiety, carboxy groups, carbalkoxy groups, preferably having up to 4 carbon atoms in the alkoxy group, carbamoyl groups, including alkyl or dialkylcarbamoyl groups, preferably having up to 4 carbon atoms in the alkyl moiety, alkylcarbonyl groups, preferably having up to 4 carbon atoms, or halo-substituted alkylcarbonyl groups, preferably having up to 4 carbon atoms. The substituted amino groups can also be heterocyclic amino groups, such as piperidino, piperazino, morpholino, pyrrolidinyl, and the like.

When Z is an alkyl group, it may be optionally substituted with a hydroxy group, a $(C_1-C_4)$alkoxy group, or a halogen atom, preferably a chlorine atom.

For the purposes of this invention, when Z is a carboxy group or a carbalkoxy group agronomically acceptable salts, esters and amides thereof are considered functionally equivalent. Examples of salts include the alkali metal, alkaline earth metal and ammonium salts such as sodium, potassium, lithium and magnesium. Examples of esters include substituted and unsubstituted alkyl esters, preferably lower alkyl esters of from 1 to 6 carbon atoms, for example, methyl, ethyl, propyl, butyl, tert-butyl, pentyl and hexyl esters wherein the substituents on the lower alkyl may be selected from alkoxy, for example, lower alkoxy such as methoxy, ethoxy, propoxy and butoxy; halo-alkoxy, for example, halo lower alkoxy such as chloroethoxy and bromoethoxy; and trihalomethylalkoxy such as trifluoromethylmethoxy. Also included are alkenyl esters of from 3 to 5 carbon atoms, for example, alkyl, propynyl, α-methylallyl and α-ethylallyl.

These novel compounds have been found to show unexpected activity as weed control agents. In a preferred embodiment of the invention, X is a halogen atom, and Z is an alkoxy group.

Examples of the compounds of the invention embraced by Formula I include:

2-chloro-α,α,α-trifluoro-p-tolyl-4-nitro-m-tolyl ether,
2-bromo-α,α,α-trifluoro-p-tolyl-3-butyl-4-nitrophenyl ether,
2,α,α,α-tetrafluoro-p-tolyl-4-nitro-3-n-propoxyphenyl ether,
2-chloro-6,α,α,α-tetrafluoro-p-tolyl-3-methylthio-4-nitrophenyl ether,
2-chloro-α,α,α-trifluoro-p-tolyl-3-propyl-4-nitrophenyl ether,
2-chloro-α,α,α-trifluoro-p-tolyl-3-ethoxy-4-nitrodiphenyl ether,
2-iodo-α,α,α-trifluoro-p-tolyl-3-ethoxy-4-nitrophenyl ether,
2,6-dichloro-α,α,α-trifluoro-p-tolyl-4-nitro-3-n-propoxyphenyl ether,
α,α,α,α',α',α'-hexafluoro-2,4-xylyl-3-n-butoxy-4-nitrophenyl ether,
2-cyano-α,α,α-trifluoro-p-tolyl-3-ethoxy-4-nitrophenyl ether,
2-chloro-6-cyano-α,α,α-trifluoro-p-tolyl-4-nitro-3-n-propoxyphenyl ether,
2-cyano-α,α,α-trifluoro-p-tolyl-3-carboxy-4-nitrophenyl ether,
2,6-dibromo-α,α,α-trifluoro-p-tolyl-3-methoxymethoxy-4-nitrophenyl ether,
2-chloro-α,α,α-trifluoro-p-tolyl-3-(2-hydroxyethoxy)-4-nitrophenyl ether,
2,α,α,α-tetrafluoro-p-tolyl-4-nitro-3-n-propylaminophenyl ether,
2-chloro-α,α,α-trifluoro-p-tolyl-3-dimethylamino-4-nitrophenyl ether,
2-cyano-α,α,α-trifluoro-p-tolyl-3-carbethoxy-4-nitrophenyl ether 2,6-dichloro-α,α,α-trifluoro-p-tolyl-3-carbethoxy-4-nitrophenyl ether
2-ethyl-α,α,α-trifluoro-p-tolyl-3-(2-carboxy ethoxy)-4-nitrophenyl ether,
α,α,α,α',α',α'-hexafluoro-2,4-xylyl-3-carbethoxymethyl-4-nitrophenyl ether,
2-cyano-α,α,α-trifluoro-p-tolyl-3-(2-carboxy propyl)-4-nitrophenyl ether,
2,α,α,α-tetrafluoro-p-tolyl-3-carbethoxymethoxy-4-nitrophenyl ether,
2-chloro-α,α,α-trifluoro-p-tolyl-3-(3,3-diethylureido)-4-nitrophenyl ether,
2-chloro-6-cyano-α,α,α-trifluoro-p-tolyl-3-acetamido-4-nitrophenyl ether,
2-chloro-α,α,α-trifluoro-p-tolyl-3-carbethoxyamino-4-nitrophenyl ether,
2-chloro-α,α,α-trifluoro-p-tolyl-3-chloro-4-nitrophenyl ether,
2-chloro-α,α,α-trifluoro-p-tolyl-3-hydroxy-4-nitrophenyl ether,
2-bromo-α,α,α-trifluoro-p-tolyl-3-butynyloxy-4-nitrophenyl ether
2-cyano-α,α,α-trifluoro-p-tolyl-3-(2-methyl)-propynyloxy-4-nitrophenyl ether,
2,6-dichloro-α,α,α-trifluoro-p-tolyl-3-(2,2,2-trifluoro)-ethoxy-4-nitrophenyl ether,
2-chloro-α,α,α-trifluoro-p-tolyl-3-(2-dimethylaminoethoxy)-4-nitrophenyl ether,
2-bromo-α,α,α-trifluoro-p-tolyl-3-acetoxy-4-nitrophenyl ether,
α,α,α,α',α',α'-hexafluoro-2,4-xylyl-3-(2-hydroxyethylamino)-4-nitrophenyl ether
α⁴,α⁴,α⁴-trifluoro-2,4-xylyl-3-amino-4-nitrophenyl ether,
2-chloro-α,α,α-trifluoro-p-tolyl-3-morpholino-4-nitrophenyl ether,
2-cyano-α,α,α-trifluoro-p-tolyl-3-(N-methylcarbamoyloxy)-4-nitrophenyl ether,
2-chloro-6,α,α,α-tetrafluoro-p-tolyl-3-propionamido-4-nitrophenyl ether,
2-chloro-α,α,α-trifluoro-p-tolyl-3-chloroacetamido-4-nitrophenyl ether,
α⁴,α⁴,α⁴-trifluoro-2,4-xylyl-3-(2,3-epoxypropoxy)-4-nitrophenyl ether,
2-chloro-α,α,α-trifluoro-p-tolyl-3-(2,3-dihydroxypropoxy)-4-nitrophenyl ether,
2-cyano-α,α,α-trifluoro-p-tolyl-3-(2-methylthioethoxy)-4-nitrophenyl ether,
2-chloro-α,α,α-trifluoro-p-tolyl-3-(1-ethyl-3-methylureido)-4-nitrophenyl ether,
2-bromo-α,α,α-trifluoro-p-tolyl-3-(2-methylsulfonylethoxy)-4-nitrophenyl ether,
α,α,α,α',α',α'-hexafluoro-2-2,4-xylyl-3-(3-methylureido)-4-nitrodiphenyl ether,
2-cyano-α,α,α-trifluoro-p-tolyl-3-ethylthiocarbonylamido-4-nitrophenyl ether,
2-cyano-α,α,α-trifluoro-p-tolyl-3-cyano-4-nitrophenyl ether,
2,6-dichloro-α,α,α-trifluoro-p-tolyl-3-carboxy-4-nitrophenyl ether,
2-chloro-α,α,α-trifluoro-p-tolyl-3-(1-carbamoylethoxy)-4-nitrophenyl ether,
2-bromo-α,α,α-trifluoro-p-tolyl-3-(3-oxobutoxy)-4-nitrophenyl ether, and the like; each compound corresponding to any of the foregoing in which the 4-trifluoromethyl group is replaced by a $C_2$, $C_3$, $C_4$, or $C_5$ 4-perfluoroalkyl or 4-partially fluorinated alkyl group, preferably a $C_2$ partially fluorinated group, more preferably a $CF_2CH_3$ group, and including specifically 2,6-dichloro-4-perfluoroethyl-3'-carbomethoxy-4'-nitrodiphenyl ether
2-cyano-4-perfluoropropyl-3'-carbomethoxy-4'-nitrodiphenyl ether,
2-bromo-4-perfluorobutyl-3'-carbomethoxy-4'-nitrodiphenyl ether,
4-perfluoropentyl-3'-carbomethoxy-4'-nitrodiphenyl ether,
2-chloro-4-perfluoroethyl-3'-carboethoxy-4'-nitrodiphenyl ether,
2,6-dichloro-4-perfluoropropyl-3'-carboxy-4'-nitrodiphenyl ether, and the sodium, potassium and ammonium salts thereof,
2-cyano-4-perfluoroethyl-3'-carboisopropoxy-4'-nitrodiphenyl ether,
2-methyl-4-perfluoroethyl-3'-methoxy-4'-nitrodiphenyl ether,
2-chloro-4-perfluoroethyl-3'-ethoxy-4'-nitrodiphenyl ether, 2,6-dichloro-4-perfluorobutyl-3'-propoxy-4'-nitrodiphenyl ether,
2-chloro-4-perfluoroethyl-3'-carboethoxymethoxy-4'-nitrodiphenyl ether,
2-chloro-4-perfluoroethyl-3'-carboxy-4'-nitrodiphenyl ether, and sodium, potassium and ammonium salts thereof,
2-chloro-4-perfluoromethyl-3'-carbomethoxy-4'-nitrodiphenyl ether,
2-chloro-4-perfluoroethyl-4'-nitrodiphenyl ether,
2-cyano-4-perfluoropropyl-3'-ethoxy-4'-nitrodiphenyl ether,
2-bromo-4-perfluoroethyl-3'-dimethylamino-4'-nitrodiphenyl ether,
2-trifluoromethyl-4-perfluoroethyl-3'-carbomethoxy-4'-nitrodiphenyl ether,
2-chloro-4-perfluorobutyl-3'-allyloxy-4'-nitrodiphenyl ether,
2-cyano-4-perfluoroethyl-3'-carboethoxymethyl-4'-nitrodiphenyl ether, and the like; and each compound corresponding to any of the foregoing in which the 4-perfluoroalkyl group is replaced by a partially fluorinated alkyl group including specifically those in which the partially fluorinated alkyl group is $-CH_2CF_3$, $-CF_2CH_3$, and $-CF_2CF_2CH_3$, and the like. The preferred partially fluorinated alkyl groups are $-CH_2CF_3$ and $CF_2CH_3$ and the $-CF_2CH_3$ group is more preferred.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period.

Among the crops on which the diphenyl ethers of the invention can be advantageously employed are, for example, cotton, soybeans, peanuts, safflower, beans, peas, carrots, corn, wheat, and other cereal crops.

Diphenyl ethers of the invention are useful for controlling weeds in rice crops. When used in transplanted rice crops, the ethers can be applied either preemergence or postemergence to the weeds—that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual".

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earch, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

Phenols dinitro-o-(sec-butyl)phenol and its salts
pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea

Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether 2,4-dichloro-3'-methoxy-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazin-(4)3H-one-2,2-dioxide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The compounds of the present invention can be made by a wide variety of conventional reaction procedures. For example, the diphenyl ethers of the invention or their precursors can be prepared by reacting a suitably substituted phenol, or the potassium or sodium salt of the phenol, with a suitably substituted halobenzene, such as a chloro or fluorobenzene, in the presence of an alkaline agent or in the Ullmann ether synthesis. Additional general procedures include the following:

(A) X and Y are as defined in formula (I) and Z is a hydroxy group, an alkoxy group, an alkyl group, a halogen atom, an amino group, an alkylthio group, a cyano group, a carboxy group or agronomically-acceptable salt thereof or a carboxyalkyl group as defined in formula I.

(1) To a frozen solution of an appropriately X and Y substituted 4-chloro or fluoro iodobenzene and copper bronze in an aprotic solvent, such as dimethylformamide (DMF), dimethylsulfoxide (DMSO), sulfolane or dioxane, is added condensed pentafluoroethyl iodide. The mixture is stirred vigorously in a glass lined pressure reactor while being warmed or heated as needed to any temperature between about 80° C. and about 225° C., depending on the solvent, preferably at about 110°–150° C. Upon completion, the copper salts are removed by filtration and the filtrate mixture is extracted with an organic solvent such as ether, methylene chloride, hexane, ethyl acetate or ethylene dichloride, and the solvents are removed under reduced pressure and the crude product is purified by distillation.

(2) The 4-chloro or fluoro pentafluoroethyl benzene above is dissolved in an organic solvent such as DMSO or DMF and an alkali metal salt of a Z-substituted m-hydroxybenzoic acid is added. The mixture is heated to a temperature of from about 80° C. to about 225° C. and 110°–180° C. is preferred. The mixture is cooled to a temperature from about −10° to about 10° C. and is acidified with a mineral acid such as hydrochloric acid or sulfuric acid. Upon completion of the reaction, the product of the formula:

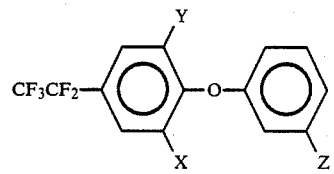

is purified as above and recrystallized from an appropriate solvent such as ethyl acetate.

(3) The X, Y, Z substituted-4-pentafluoroethyl diphenylether is nitrated in the presence of a source of nitrate ion such as, nitric acid, potassium nitrate or nitronium tetrafluoroborate and a strong acid such as concentrated sulfuric acid, while maintaining the temperature of the mixture between about −10° C. and 50° C. Upon completion of the reaction, the product is purified as above and, if required, is recrystallized from an appropriate solvent.

(4) In the instance where Z above is a carboxy group, a diphenylether of the invention wherein Z is a carbalkoxy group can be readily obtained by reacting the 2-nitro-5-(X,Y-4-pentafluoroethylphenoxy)benzoic acid with an alkylhalide such as methyliodide, either neat or in the presence of an aprotic solvent such as DMSO or DMF, in the presence of an alkali base such as sodium or potassium hydroxide, bicarbonate or carbonate at any temperature between about 0° C. to about 35° C.

(B) X, Y and Z are as defined for reaction procedure (A) above.

(1) To an appropriately X, Y-substituted-4-chloro or fluoro or nitro-benzaldehyde neat or in an organic solvent such as methylene chloride, ether, 1,2-dimethoxyethane or ethylene dichloride, is added a dialkylaminosulfurtrifluoride such as diethylaminosulfurtrifluoride. The mixture is allowed to remain at room temperature until the fluorination is completed. The X, Y-substituted-4-chloro or fluoro or nitro-difluoromethylbenzene is extracted with an appropriate organic solvent such as a halocarbon and purified by distillation.

(2) The difluoromethylbenzene product from (B)(1) is then reacted in the manner described in (A)(2) above to obtain the product of the formula:

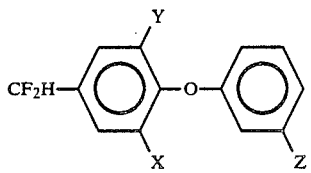

which can then be further reacted as described in (A)(3) and (4) above or reacted with diazomethane, for example, in the manner described in Example 3(C), infra, to obtain the methylbenzoate product which is then nitrated, for example, as described in (A)(3) above.

(C) X is a chloro atom, Y is as defined in formula (I) and Z is a hydroxy group, an alkoxy group, an alkyl group, a halogen atom, an amino group, an alkylthio group, a cyano group, a carboxy group or an agronomically acceptable salt thereof, a carbalkoxy group, a carbalkoxyalkyl group, an alkanoyloxy group or a carbamoyloxy group.

(1) Chlorine gas is bubbled through a solution of Y-substituted-p-hydroxyacetophenone dissolved in an organic solvent such as methylene chloride, ethylene dichloride or ether at a temperature between about 10° C. and 50° C., preferably at a temperature of $-10°-5°$ C. The resulting X-chloro-Y-substituted p-hydroxyacetophenone precipitates from the solution and can be collected by filtration.

(2) A base such as sodium or potassium hydride or hydroxide either neat or in a organic solvent such as ether or tetrahydrofuran is added to the X-chloro-Y-substituted-3-chloro-4-hydroxyphenone above which is dissolved in an organic solvent such as ether or tetrahydrofuran. The solvent is stripped off and an organic solvent such as sulfolane, dimethylsulfoxide or N,N-dimethylformamide, is added to the resulting powder. A Z-substituted-2-nitro-5-fluorobenzene is added and the mixture is heated to any temperature between about 60° C. and 225° C., preferably between 80° and 120° C. Upon completion, the product is extracted with an organic solvent such as ether, methylene chloride or ethylacetate. The volatiles are removed under reduced pressure and the final product is recrystallized from an appropriate solvent such as propanol, chloroform or ether.

(3) The resulting product of the formula:

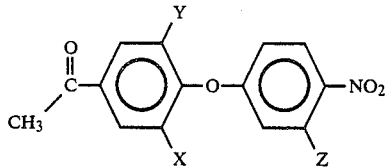

is dissolved in an appropriate solvent such as 1,2-dimethoxyethane (DME), tetrahydrofuran or ether and cooled to a temperature of between about $-10°$ C. and 10° C. Thereafter, a dialkylaminosulfurtrifluoride is slowly added with stirring. The mixture is heated to any temperate between about 30° and 85° C., preferably between 80° and 85° C. After pouring the cooled reaction mixture onto ice water, the product is extracted with an appropriate organic solvent and purified, for example, by gravity columns.

EXAMPLES

The following examples will further illustrate this invention but are not intended to limit it in any way.

EXAMPLE 1

Preparation of 2-nitro-5-(2-chloro-4-pentafluoroethylphenoxy)benzoic acid

A. 3′,4′-dichloropentafluoroethylbenzene

An autoclave was charged with 9.33 gm (34.2 mmol) of 3,4-dichloroiodobenzene, 8.64 gm of activated copper bronze powder and 42 ml of anhydrous dimethylformamide (The copper bronze powder (40 gm) was activated by stirring for 15 minutes with 500 ml of a 2% (w/v) solution of iodine in acetone, collecting the metal by filtration, then stirring it for 15 minutes with a 50% (v/v) solution of concentrated hydrochloric acid in acetone, collecting the metal by filtration and drying it). The contents of the autoclave were frozen under nitrogen atmosphere in a dry ice isopropanol bath. 15.0 gm (61 mmol) of condensed pentafluoroethyl iodide were added. The autoclave was sealed and pressurized to 60 psig with nitrogen gas and allowed to warm to room temperature. The contents of the autoclave were stirred vigorously while heating to 120° C. and held at this temperature for 3.5 hours. After cooling to about $-78°$ C. the nitrogen in the vessel was vented and the contents allowed to warm to room temperature. The autoclave was opened and the contents diluted with 150–200 ml of ether. Solid copper salts were removed by filtration through Celite (diatomaceous earth), the filtrate washed with water and then with a saturated sodium chloride solution. The ether was concentrated in a rotary evaporator yielding a yellow oil which on distillation (95°–120° C. at 760 mm) gave 6.0 gm (66.4%) of colorless 3′,4′-dichloropentafluoroethylbenzene having an elemental analysis, calculated (found): C: 45.73 (46.22); H: 1.92 (2.04); Cl: 7.64; F: 25.84; N: 3.81 (4.24); O: 13.06; and $^{19}F\text{-nmr} = -85.2$ ppm, $-115.4$ ppm, $CFCl_3$.

B. 3-(2-chloro-4-pentafluoroethylphenoxide)benzoic acid 1.57 gm (11.4 mmol) of m-hydroxybenzoic acid in 15.0 ml of anhydrous tetrahydrofuran were added dropwise to a suspension of 550 mg (22.8 mmol) of sodium hydride (prewashed with pentane to remove oil) in 20 ml of tetrahydrofuran (THF). Thereafter, 40–50 ml of THF were added to break up the emulsion which had formed. After stirring for 1 hour the tetrahydrofuran was removed under a vacuum leaving a white powder of disodium salt of m-hydroxybenzoic acid which was suspended in 45 ml of freshly distilled (from barium oxide) dimethylsulfoxide. To this were added 3.00 gm (11.4 mmol) of 3,4-dichloropentafluoroethylbenzene and the flask heated to 140° C. for 3 hours.

The cooled mixture was poured onto ice and carefully acidified with concentrated hydrochloric acid. The diphenyl ether acid was twice extracted with ether, the combined organic extracts were washed with saturated sodium chloride solution, dried and evaporated to a light yellow oil which crystallized on standing at room temperature. The yield was 3.50 gm (83.8%). The crude acid was crystallized from ethyl acetate and had a melting point range of 102°–105° C. and an elemental analysis, calculated (found): C: 49.14 (51.19); H: 2.20 (2.67); Cl: 9.67 (7.25); F: 25.91 (22.39); O: 13.09.

C. 2-nitro-5-(2-chloro-4-pentafluoroethylphenoxy)benzoic acid

A 50 ml 3-neck round bottom flash was charged with 2.5 gm (6.83 mmol) of 3-(2-chloro-4-pentafluoroethylphenoxy)benzoic acid, 2.18 gm (2.08 ml, 36.19 mmol) of glacial acetic acid, 2.1 gm (20.49 mmol) of acetic anhydride and 70 mg (683 mmol) of concentrated sulfuric acid. The resulting slurry was stirred vigorously while cooling to 0°–5° C. with the aid of an icewater bath. To the cooled slurry was added dropwise a mixture 280 mg (2.73 mmol) of concentrated sulfuric acid and 620 mg (9.56 mmol) to 97% nitric acid (red fuming). The yellow solution was maintained at 0°–5° C. for about 1.5 hours at which time the reaction mixture was poured into stirred ice water. The gummy residue that formed in the bottom of the flask was extracted with 100 ml of ether, the ether layer separated, and the aqueous acid layer reextracted with a second portion of ether. The combined ether layers were washed with brine, dried and evaporated in vacuo leaving a yellow oil. Much of the yellow color was removed by dissolving the oil in 300 ml of chloroform and eluting through a pad of silica gel. Evaporation of the eluent yielded 2.36 gm (83.9%) of a light yellow oil which crystallized on standing. The product had the following elemental analysis, calculated (found): C: 43.76 (44.43); H: 1.71 (2.24); Cl: 8.61 (8.83); F: 23.07 (18.90); N: 3.40 (2.47); O: 19.43.

EXAMPLE 2

Preparation of Methyl 2-nitro-5-(2-chloro-4-pentafluoroethylphenoxy)benzoate 390 mg (2.76 mmol) of methyl iodide and 320 mg (2.3 mmol) of powdered potassium carbonate were added to 940 mg (2.3 mmol) of 2-nitro-5-(2-chloro-4-pentafluoroethylphenoxy)benzoic acid in 30 ml of dimethylforamide (freshly eluted through neutral alumina). After 1 hour, the mixture was poured into 300 ml of water, extracted with ether, the ether layer was washed with saturated sodium chloride solution, then dried and evaporated to 820 mg of light yellow oil (84%) diphenyl ether methyl benzoate having the following elemental analysis, calculated (found): C: 45.14 (47.54); H: 2.13 (2.69); Cl: 8.33 (6.19); F: 22.31 (21.26); N: 3.29 (2.72); O: 18.79.

pmr (CDCl$_3$, 60 mHz): 4.00 ppm (s) 3H COOCH$_3$; 7.10–7.96 ppm (m) 5H aromatics; 8.2 ppm (d J=10 Hz) 1H o-NO$_2$ aromatic.

EXAMPLE 3

Preparation of methyl-2-nitro-5-(2-chloro-4-difluoromethylphenoxy)-benzoate

A. 3,4-dichloro-α,α-difluorotoluene

A 300 ml 3-neck round bottom flask was fitted with a rubber septum, nitrogen gas inlet and a glass stopper. The flask was charged with 10.0 gm (57.1 mmol) of 3,4-dichlorobenzaldehyde and 50 ml of methylene chloride. 7.15 ml (57.1 mmol) of diethylaminosulfur trifluoride were added over a period of 5 to 10 minutes. Fluorination was completed in 2 to 8 hours. The crude 3,4-dichloro-α,α-difluorotoluene mixture was poured onto ice and the organic layer separated. The aqueous layer was extracted with a second portion of methylene chloride. The combined organic extracts were washed with water, dried and evaporated in vacuo. The resulting crude oil was transferred to a flask and fitted for distillation through a Vigreux column and a short path condenser. The 3,4-dichloro-α,α-difluorotoluene was collected as a fraction which distilled at 95°–105°/90 mm. The yield was 9.3 gm (83.1%) having an elemental analysis calculated (found) to be: C: 42.68 (42.54); H: 2.05 (2.15); Cl: 35.99 (34.55); F: 19.29 (19.12).

B. 3-(2-chloro-4-difluoromethylphenoxy)benzoic acid 730 mg (30.4 mmol) of sodium hydride (washed with pentane to remove the oil) were suspended in 25 ml of freshly dried tetrahydrofuran (THF). 2.11 gm (15.2 mmol) of m-hydroxy benzoic acid in 20 ml of dry THF were added dropwise to the sodium hydride suspension via an addition funnel. An additional 50–60 ml of THF was added to the resulting milky suspension. A rotary evaporator, under a vacuum, was used to remove the THF after the evolution of hydrogen gas was complete.

The resulting off-white powder was resuspended in 110 ml of dimethylsulfoxide (DMSO) (freshly eluted through neutral alumina) and 3.0 gm (15.2 mmol) of 3,4-dichloro-α,α-difluorotoluene were added. The brownish mixture was heated in an oil bath at 130° C. for about 15 hours. The mixture was cooled to ambient temperature, poured into 500 ml of ice-cold 1N hydrochloric acid. The crude phenoxybenzoic acid was extracted with 150 ml of methylene chloride, the organic layer separated, washed with saturated sodium chloride solution, dried and evaporated in vacuo.

The excess DMSO that remained was removed by redissolving the oil in approximately 150 ml of ether and washing the ether with saturated sodium chloride solution, drying and evaporating to 2.6 gm (58%) of a yellow solid having the following elemental analysis, calculated (found): C: 56.30 (54.27); H: 3.04 (3.07); Cl: 11.87; F: 12.72 (13.16); O: 16.07.

C. Methyl 3-(2-chloro-4-difluoromethylphenoxy)benzoate

Into a distilling flask of a diazomethane generator were placed 5.9 gm potassium hydroxide, 8 ml of water, and 25 ml of absolute ethanol dissolved in about 100 ml of ether. About 22.2 gm of p-tolylsulfonylmethylnitrosamide were dissolved in approximately 200 ml of ether and placed in the dropping funnel of the generator. The temperature of the alcoholic base was raised to 60°–65° C. while adding to it the ethereal nitrosamide.

As the diazomethane was produced, it was pipetted into the flask containing 18 gm (60 mmol) of 3-(2-chloro-4-difluoromethylphenoxy)benzoic acid dissolved in 100 ml of ether. Upon completion, the reaction solution was gravity filtered and the ether was stripped off yielding 17.65 gm of a golden brown oil which was run through a silica gel column resulting in 4 gm of a yellow oil containing methyl 3-(2-chloro-4-difluoromethylphenoxy)benzoate.

D. Methyl-2-nitro-5(2-chloro-4-difluoromethylphenoxy)benzoate

This product was nitrated using the procedure described for the nitration of 3-(2-chloro-4-pentafluoromethylphenoxy)benzoic acid (Example 1) to obtain methyl-2-nitro-5-(2-chloro-4-difluoromethylphenoxy)benzoate which had the following elemental analysis, calculated (found): C: 50.37 (47.50); H: 2.82 (2.68); Cl: 9.91 (20.73); F: 10.62 (14.18); O: 22.36.

pmr (60 MHz, CDCl$_3$): 4.00 ppm, (s), 3H, COOCH$_3$; 6.76 ppm, (t, J=56 Hz) 1H, —CF$_2$H; 6.98–8.22 pm (m) 6H, aromatics.

EXAMPLE 4

Preparation of
Methyl-2-nitro-5-[2-chloro-4(α,α-difluoroethyl)-phenoxy]benzoate

A. 3-chloro-4-hydroxy acetophenone 50 gm of p-hydroxyacetophenone were dissolved in 500 ml of hot methylene dichloride and filtered through a small pad of silica gel. The solution was allowed to cool and the methylene dichloride was stripped off to obtain 41.75 gm (0.31 mol) of crystals. These crystals were dissolved in about 1.5 liters of methylene dichloride. The reaction flask was placed in an ice bath and chlorine gas was bubbled through the solution. After about a total of 5 minutes of $Cl_{2(g)}$ bubbling, the methylene chloride was stripped off to yield more than 30 gm of white crystals (>90% pure) of 3-chloro-4-hydroxy acetophenone.

B. Methyl-2-nitro-5-(2-chloro-4-acetylphenoxy)benzoate 5.37 gm of 86.4% (82.7 mmol) of potassium hydroxide were dissolved in 600–700 ml of methanol. 14.12 gm (82.7 mmol) of 3-chloro-4-hydroxy acetophenone were dissolved in about 150 ml of methanol and added to the stirring methanolic potassium hydroxide. The methanol was stripped off and the resulting powder was suspended in sulfolane. 16.48 gm (82.7 mmol) of methyl-2-nitro-5-fluoro benzoate were added to the mixture. While stirring, the reaction was heated to reflux and left overnight.

The resulting dark brown liquid was poured into water and extracted three times with ether. The combined organic layers were further washed with brine and potassium carbonate solution. The dried ether was filtered through silica gel and concentrated on a rotoevaporator. Recrystallization from 2-propanol, yielded 12.6 gm of yellow-brown solid (>90% pure) of the methyl benzoate.

C. Methyl-2-nitro-5[2-chloro-4-(α,α-difluoroethyl)-phenoxy]benzoate 40 gm (114 mmol) of the acetophenone from step B were dissolved in approximately 400 ml of freshly distilled dimethoxyethane (DME). This mixture in its reaction flask was placed in an ice bath. 21.4 ml (171 mmol) of diethylaminosulfur trifluoride (DAST) were added slowly to the cool, stirring solution. Upon completion of the addition of the DAST, the flask was heated to a very, very gentle reflux for about 20–24 hours. Then a second aliquoit of DAST was added, and refluxing continued another 20 hours.

The reaction was quenched by slowly adding the cooled flask to water. The product was extracted with ether and the organic layer collected after removing an emulsion by filtration. The organic layer was again washed with water, brine, dried and concentrated.

Purification was accomplished using two successive gravity columns, yielding 20 gm of solid (approximately 93% pure) methyl-2-nitro-5[2-chloro-4-(α,α-difluoroethyl)phenoxy]benzoate.

EXAMPLE 5

Preparation of
2-nitro-5[2-chloro-4-(α,α-difluoroethyl)phenoxy]benzoic acid 8 gm (21.5 mmol) of methyl-2-nitro-5-[2-chloro-4-(α,α-difluoroethyl)phenoxy]benzoate were placed in 150–200 ml of dry dimethyl formamide (DMF). 3.17 g (23.65 mmol) of lithium iodide were added to the stirring solution. This mixture was heated to reflux for about 12 hours.

The reaction mixture was cooled, poured into water and acidified to pH 1 using concentrated hydrochloric acid. The product was extracted with ether. The ether was stripped off using a rotoevaporator, yielding an oil (approximately 93% pure) of 2-nitro-5-[2-chloro-4-(α,α-difluoroethyl)phenoxy]benzoic acid.

EXAMPLE 6

Preparation of
2-chloro-4-α,α-difluoroethyl-3'-methoxy-4'-nitrodiphenyl ether

A. 3-Chloro-4-fluoroacetophenone 53.2 gm. (400 mmol) of aluminum chloride was carefully added in portions to a mixture of 26.2 gm (200 mmol) of 1-chloro-2-fluorobenzene and 31.2 gm of acetyl chloride at 50° C. After all the Lewis acid had been added, the reaction temperature was raised to 100° C. and maintained at that temperature for 3 hours. The hot reaction mixture was carefully poured onto ice and the resulting light-red oil twice extracted with ether. The combined ether extraacts were washed with saturated sodium chloride solution, dried and evaporated in vacuo to yield a crude brown oil. The oil was distilled to yield 26.47 gm of colorless oil.

pmr (90 mHz, CDCl$_3$): 2.60 ppm (s, 3H), COCH$_3$); 7.14–8.15 ppm (m, 3H), aromatics B. 3-Chloro-4-(3'-methoxyphenoxy)acetophenone A 250 ml round bottom flask was charged with 6.4 gm (37 mmol) of 3-chloro-4-fluoroacetophenone, 4.60 gm (37 mmol) of 3-methoxyphenol and 50 ml of DMF. To the solution was added 5.11 gm (37 mmol) of potassium carbonate. The mixture was refluxed for about 12 hours, cooled to room temperature, poured onto 100 ml of ice water and twice extracted with ether. The combined organic layers were washed with saturated solution of sodium chloride, dried and evaporated in vacuo to yield 9.5 gm (93%) of a light brown oil.

pmr (90 mHz, CDCl$_3$): 2.60 ppm (s, 3H), COCH$_3$; 3.80 ppm (s, 3H); OCH$_3$; 6.40–8.20 ppm (m, 7H), aromatics B. 3-Chloro-4-(3'-methoxy-4'-nitrophenoxy)acetophenone A 250 ml. 3-neck round bottom flask was fitted with a thermometer, drying tube (calcium chloride) and 10 ml addition funnel. The flask was charged with 21.5 gm (78 mmol) of 3-chloro-4-(3'-methoxyphenoxy)acetophenone, 50 ml of methylene chloride and 35 gm (342 mmol) of acetic anhydride. The solution was cooled to 10° C. with the aid of an ice water bath and 2.3 gm of concentrated sulfuric acid were added dropwise. The addition funnel was then charged with 10.2 gm of 70% aqueous nitric acid which was added dropwise to the stirred acetophenone solution. The temperature of the reaction was monitored to prevent it from exceeding about 20° C. during the addition of the nitric acid. The reaction mixture was immediately poured into 400 ml of ice water and the crude nitrodiphenyl ether was twice extracted with methylene chloride. The organic extracts were combined, washed with cold saturated sodium bicarbonate solution, water, dried and evaporated in vacuo. The resulting crude dark brown oil (26.2 gm) was partially decolorized by boiling with carbon as a 1:1 hexanes:methylene chloride solution and then filtered hot through Celite (diatomaceous earth). The filtrate was evaporated and the resulting oil was purified by column chromatography (200 gm silica gel, eluted with 4/1, hexanes/ethyl acetate) yielding 6.27 gm (25%) of cream colored crystals which were crystallized from ethylacetate.

mp 122°–126° C., pmr 90 mHZ, CDCl$_3$: 2.60 ppm (S, 3H), COCH$_3$; 3.94 ppm (S, 3H), OCH$_3$; 6.45–8.22 ppm (m, 6H), aromatics.

D. 2-Chloro-4-α,α-difluoroethyl-3'-methoxy-4'-nitrodiphenylether 3.27 gm (10.2 mmol) of the 4-acetylnitrodiphenyl ether in 100 ml of anhydrous dimethoxyethane (freshly distilled from benzophenone ketyl) was treated with 6.0 ml (48 mmol) of diethylaminosulfur trifluoride (DAST). The solution was heated at reflux under nitrogen atmosphere for about 20 hours. The reaction mixture was cooled to ambient temperature and carefully poured onto ice. The crude difluoroethylnitrodiphenylether was extracted twice with ether. The extracts were combined, washed with water, saturated sodium chloride solution, dried and evaporated in vacuo to 3.1 gm crude brown oil.

The residue was purified by silica gel column chromatography (75 gm silica gel, eluted with 8:1 hexanes to ethylacetate, affording 1.2 gm (35%) of colorless oil.

Elemental analysis, calculated (found): C: 52.41 (47.87), H: 3.52 (3.37), Cl: 10.32 13.58), F: 11.06 (9.50), N: 4.08 (4.11), O: 18.62.

pmr (90 mHz, CDCl$_3$): 1.98 ppm (t, J—19 Hz, 3H), CF$_2$CH$_3$; 3.94 ppm (S, 3H), OCH$_3$; 6.50–8.24 ppm (m, 6H), aromatics. fmr (90 mHz, CDCl$_3$, CCl$_3$F standard): —87.526 ppm (q, J=20.5 Hz) —CF$_2$CH$_3$.

Table 1 summarizes the structure of the compounds prepared in Examples 1–6.

TABLE 1

C$_n$H$_m$F$_p$—[ring with X top, Y bottom]—O—[ring with Z top, NO$_2$ right]

| Example | X  | Y | Z      | n | m | p |
|---------|----|---|--------|---|---|---|
| 1       | Cl | H | COOH   | 2 | 0 | 5 |
| 2       | Cl | H | COOCH$_3$ | 2 | 0 | 5 |
| 3       | Cl | H | COOCH$_3$ | 1 | 1 | 2 |
| 4       | Cl | H | COOCH$_3$ | 2 | 3 | 2 |
| 5       | Cl | H | COOH   | 2 | 3 | 2 |
| 6       | Cl | H | OCH$_3$ | 2 | 3 | 2 |

It should be noted that the diphenyl ethers of the invention can also be named correctly using different systems of nomenclature. However, within the specification and claims of this invention the system of nomenclature exemplified in the examples has been followed.

EXAMPLE 7

This example shows the herbicidal activity of diphenyl ethers of the invention towards a number of common weeds. Using the procedure described below, diphenyl ethers were evaluated for control of the following weeds:

Monocots
barnyardgrass (*Echinochloa crusgalli*)
downy brome (*Bromus tectorum*)
foxtail (*Setaria faberii*)
Johnsongrass (*Sorghum halepense*)
nutsedge (*Cyperus esculentus*)
quackgrass (*Agropyron repens*)
wild oats (*Avena fatua*)
Dicots
cocklebur (*Xanthium pensylvanicum*)
marigold (Tagetes spp.)
morningglory (Ipomoea spp.)
sicklepod (*Cassia obtusifolia*)
tomato (*Lycopersicon esculentum*)
velvetleaf (*Abutilon theophrasti*)

The following test procedure was employed. Seeds of selected crops and weeds were planted in soil in flats. For preemergence tests, the flats were treated with the test compound immediately after the planting. For postemergence tests, the seeds were allowed to germinate, and after two weeks the flats were treated with the test compound. The compounds to be evaluated were dissolved in acetone, diluted with water, and sprayed over the flats using a carrier volume equivalent to 50 gallons per acre at the rate indicated in Table 2. About two weeks after the application of the test compound, the state of growth of the plants was observed and the phytotoxic effect of the compound was evaluated. Table 2 gives the average percent control against the aforementioned monocots (AM) and dicots (AD) achieved by the test compounds in terms of the percent of the plants which were killed by the compounds.

TABLE 2

|          | Rate | Preemergence | | Postemergence | |
|----------|------|------|------|------|------|
| Compound | lb/A | AM | AD | AM | AD |
| 1 | 2 | 30 | 48 | 11 | 33 |
| 2 | 4 | 75 | 89 | 37 | 79 |
| 3 | 2 | 78 | 83 | 50 | 92 |
| 4 | 2 | 83 | 88 | 86 | 97 |
| 5 | 2 | 83 | 66 | 58 | 87 |
| 6 | 2 | 79 | 84 | 36 | 71 |

What is claimed is:

1. A compound of the formula:

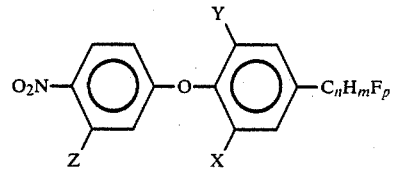

wherein
n is an integer of from 2 through 5,
m is an integer of from 0 through 2n,
p is an integer of from 1 through 2n+1, and wherein m+p=2n+1,
X is a hydrogen atom, a halogen atom, a trifluoromethyl group, a (C$_1$–C$_4$)alkyl group, or a cyano group,
Y is a hydrogen atom, a halogen atom, or a trifluoromethyl group, and
Z is a hydroxy group, an alkoxy group having up to 6 carbon atoms, an alkyl group having up to 4 carbon atoms, a halogen atom, an amino group, an alkylthio group having up to 4 carbon atoms, a cyano group, a carboxy group, a carbalkoxy group having up to 4 carbon atoms in the alkoxy moiety, a carboxyalkyl group having up to 4 carbon atoms, a carbalkoxyalkyl group having up to 6 carbon atoms, an alkanoyloxy group having up to 4 carbon atoms, or a carbamoyloxy group having up to 6 carbon atoms.

2. The compound of claim 1 wherein n is 2, Y is a hydrogen atom, and X is a halogen atom.

3. The compound of claim 2 wherein X is a chloride atom.

4. The compound of claim 3 wherein Z is a carboxy, carbalkoxy or alkoxy having up to six carbon atoms.

5. The compound of claim 4 wherein Z is a carbomethoxy or carboethoxy group.

6. The compound of claim 4 wherein Z is a sodium, potassium or ammonium salt of the carboxy group.

7. The compound of claim 1 wherein m is 3, n is 2, p is 2, X is a hydrogen or chloride atom, Y is a chloride atom and Z is a carbomethoxy group.

8. A compound of the formula:

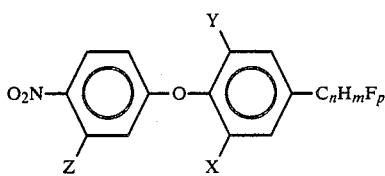

wherein
n is an integer of 2 or 3,
m is an integer of from 0 to 2n,
p is an integer of from 1 through 2n+1 and wherein m+p=2n+1,
X is a hydrogen atom, a halogen atom, a trifluoromethyl group, a ($C_1$-$C_4$)alkyl group, or a cyano group,
Y is a hydrogen atom, a halogen atom, or a trifluoromethyl group, and
Z is a hydroxy group, an alkoxy group having up to 6 carbon atoms, an alkyl group having up to 4 carbon atoms, a halogen atom, an amino group, an alkylthio group having up to 4 carbon atoms, a cyano group, a carboxy group, a carbalkoxy group having up to 4 carbon atoms in the alkoxy moiety, a carboxyalkyl group having up to 4 cabon atoms, a carbalkoxyalkyl group having up to 6 atoms, an alkanoyloxy group having up t 4 carbon atoms, or a carbamoyloxy group having up to 6 carbon atoms.

9. The compound of claim 8 wherein m is 3, n is 2, and p is 2.

10. A compound of the formula:

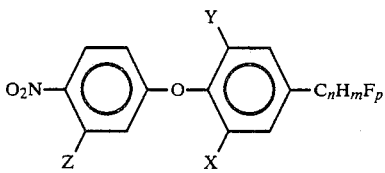

wherein
m is 2 or 3,
n is 2 or 3,
p is 2 or 4 and wherein m+p=2n+1,
X is a hydrogen atom, a halogen atom, a trifluoromethyl group, a ($C_1$-$C_4$)alkyl group, or a cyano group, Y is a hydrogen atom, a halogen atom or a trifluoromethyl group, and
Z is a hydroxy group, an alkoxy group having up to 4 carbons, a carboxy group having up to 4 carbons, a carbalkoxy group having up to 4 carbon atoms in the alkoxy moiety, a carboxyalkyl group having up to 4 carbon atoms, or a carbalkoxyalkyl group having up to 6 carbon atoms.

11. The compound of claim 10 wherein m is 3, n is 2, and p is 2.

12. The compound of claim 11 wherein the —$C_nH_mF_p$ is —$CF_2CH_3$.

13. The compound of claim 12 wherein X is a chlorine atom, Y is a hydrogen or chlorine atom and Z is a carboxy group or a salt thereof, a carbalkoxy group or a salt thereof, a carboxyalkyl group or a carbalkoxyalkyl group.

14. The compound of claim 13 where X is a chlorine atom, Y is a hydrogen or chloride atom, Z is a carboxy group, a carbomethoxy group, a carboethoxy group, or a sodium, potassium, or ammonium salt thereof, a methoxy group or an ethoxy group.

15. The compound of claim 14 selected from the group consisting of methyl 2-nitro-5-(2-chloro-4-(alpha,alpha-difluoroethyl)phenoxy)benzoate, 2-nitro-5-(2-chloro-4-(alpha,alpha-difluoroethyl)phenoxy)benzoic acid and the sodium, potassium or ammonium salt thereof.

16. The compound of claim 15 which is methyl 2-nitro-5-(2-chloro-4-(alpha,alpha-difluoroethyl)phenoxy)benzoate or the sodium, potassium or ammonium salts thereof.

17. A herbicidal composition comprising a herbicidally-effective amount of the compound of claim 1 and an agronomically-acceptable carrier.

18. A herbicidal composition comprising a herbicidally effective amount of the compound of claim 10 and an agronomically-acceptable carrier.

19. A method of controlling weeds which comprises applying to the surface of the growth medium prior to the emergence of the weeds from the growth medium the compound of claim 10 wherein
X is a hydrogen atom, a halogen atom, a trifluoromethyl group, or a ($C_1$-$C_4$)alkyl group,
Y is a hydrogen atom, a halogen atom, or a trifluoromethyl group, and
Z is a carboxy group, a carbalkoxy group having up to 4 carbon atoms, or a carbalkoxyalkyl group having up to 6 carbon atoms,
in an amount sufficient to control the growth of the weeds.

20. A method of controlling weeds which comprises applying to weed seedlings a compound according to claim 10 wherein
X is a hydrogen atom, a halogen atom, a trifluoromethyl group, or a ($C_1$-$C_4$)alkyl group,
Y is a hydrogen atom, a halogen atom, or a trifluoromethyl group, and
Z is a carboxy group, a carbalkoxy group having up to 4 carbon atoms in the alkoxy moiety, a carboxyalkyl group having up to 4 carbon atoms, or a carbalkoxyalkyl group having up to 6 carbon atoms,
in an amount sufficient to control the growth of the seedlings.

* * * * *